United States Patent [19]

Mirabel et al.

[11] 4,258,133

[45] Mar. 24, 1981

[54] ENZYME-SUPPORT COMPLEXES

[75] Inventors: Bernard Mirabel, Orly; Francois Meiller, Palaiseau, both of France

[73] Assignee: Rhone-Poulenc Industries, Paris, France

[21] Appl. No.: 12,394

[22] Filed: Feb. 15, 1979

[30] Foreign Application Priority Data

Feb. 16, 1978 [FR] France ............................... 78 04354
Jan. 23, 1979 [FR] France ............................... 79 01580

[51] Int. Cl.³ .............................................. C12N 11/14
[52] U.S. Cl. ..................................... 435/176; 435/181
[58] Field of Search ................................. 435/176, 181

[56] References Cited

U.S. PATENT DOCUMENTS

| | | | |
|---|---|---|---|
| 3,519,538 | 7/1970 | Messing et al. | 435/176 |
| 3,669,841 | 6/1972 | Miller | 435/176 |
| 4,034,139 | 7/1977 | Mazarguil et al. | 435/176 X |
| 4,119,494 | 10/1978 | Durand et al. | 435/176 |

*Primary Examiner*—David M. Naff

[57] ABSTRACT

Enzyme-support complexes in which the enzymes are bound by covalent bonding to at least one reactive function of organic groups grafted to mineral supports by at least one ester bond. The complexes are obtained by reacting an insoluble inorganic support having hydroxyl groups with a compound formed of an organic group having at least one alcohol or phenol function and at least one reactive function, to which the enzyme is then bonded.

12 Claims, No Drawings

ENZYME-SUPPORT COMPLEXES

BACKGROUND OF THE INVENTION

The object of the invention is novel, active, stable enzyme-support complexes, as well as a novel method of manufacturing them.

It is known to immobilize enzymes on supports having groups which are reactive with the enzymes. These are, for instance, celluloses, polysaccharides, or inorganic solids, which are modified by different techniques, such as adsorption of various compounds, coating with polymers, or grafting of silanes in order to provide them with the necessary reactive groups. However, the cellulose and polysaccharides do not have satisfactory mechanical properties; they swell in water and organic solvents and do not withstand variations in temperature and pressure. Moreover, enzymes adsorbed or deposited on the support run the risk of being eliminated during the subsequent use. As for the silanes, they are very special products of high price which do not always provide satisfactory results.

On the other hand, the enzyme-support complexes of the invention are particularly stable. They have a base of grafted inorganic supports which have excellent mechanical properties, they are insensitive to most solvents, temperature, and pressure. The grafts, furthermore, are of ordinary organic compounds.

It is an object of the present invention to provide enzyme-support complexes which are stable, and the support of which has excellent mechanical properties, and are insensitive to most solvents, temperature, and pressure.

It is a further object to provide a novel method of preparing the enzyme-support complexes of the invention.

Further objects will be apparent to those skilled in the art from the present description.

GENERAL DESCRIPTION OF THE INVENTION

The stable, enzymatically active enzyme-support complexes of the invention are formed of enzymes attached by covalent bonding to a grafted inorganic support, and they are characterized by the fact that the enzymes are bound to at least one reactive function of organic groups grafted to the supports by at least one ester bond.

The said organic groups are represented, more particularly, by linear or branched aliphatic radicals whose chain, consisting of about 1 to 8 carbon atoms, may contain a nitrogen atom and/or a sulfur atom and/or a phenyl group; cyclane radicals; aryl or alkaryl radicals whose ring and/or chain may contain one or more nitrogen atoms. As function reactive with the enzyme, mention may be made, more particularly, of the amine, halogen, sulfhydryl, aldehyde, and carboxyl functions.

The complexes in accordance with the invention are obtained by the process of the invention, which comprises reacting an insoluble inorganic support, having hydroxy groups, with a compound formed of an organic group having at least one alcohol or phenol function and at least one reactive function, to which the enzyme is then bound.

The inorganic support used must be practically and substantially insoluble in water and have surface hydroxyl groups. It may be in the form of blocks, pieces, balls, beads, objects, threads, or fabrics whose surfaces may or may not be porous, the selection of the support being a function of the use of the complex. For example, when the enzyme-support complex is used in a continuously operating column, it is advantageous for the finely divided support to have a particle size of between 5 $\mu$m and 5 mm. As to the porosity of the support, it is a function of the enzymatic activity of the complex, the activity being greater the greater the accessible internal surface.

The inorganic support is represented, more particularly, by brick, alkaline silicates and aluminosilicates, metallic oxides, such as the aluminas and titanium dioxide, and the silicas.

The organic compound is an alcohol or phenol whose functions, which are reactive with the enzyme, namely, amino, halogen, sulfhydryl, aldehyde, or carboxyl and the —OH (hydroxyl) functions, are bound to one of:

(1) linear or branched aliphatic radicals whose chain, comprising about 1 to 8 carbon atoms, which may optionally contain a nitrogen atom and/or a sulfur atom and/or a phenyl group. Among such compounds, mention may be made of the amino alcohols, such as monoethanolamines, aminopropanols, aminomethylpropanols, phenylamino propanols, aminobutanols, aminopentanols, aminomethyl heptanols, aminoethyl ethanolamine, methioninol, aminomethyl propanediol, tris hydroxymethyl aminomethane, hydroxymethylanilines, tryptophanol; the haloalcohols, such as chloroethanols, chloropropanols, chloromethylpropanols, chlorobutanols, chlorohexanols, chloropropanediols, chlorobenzylic alcohols, bromoethanols, bromopropanols, bromopropanediols, bromobenzylic alcohols, bromobenzhydrols, iodoethanols; the mercaptoalcohols, such as mercaptoethanols, thioglycerols, dithioerythritols; the alcohol aldehydes, such as glyceraldehydes; the alcohol acids, such as hydroxypropionic, hydroxybutyric, hydroxyvaleric, hydroxycaproic, hydroxyoctanoic, and hydroxymethylbenzoic acids;

(2) cyclane radicals, such as the aminocyclohexanols;

(3) aryl or alkylaryl radicals whose ring and/or chain may contain one or more nitrogen atoms. These comprise, for instance, the aminophenols, such as aminophenols, aminocresols, aminohydroxypyridines, aminohydroxypyrimidines, aminodihydroxypyrimidines, aminohydroxymethylpyrimidines; the halophenols, such as chlorophenols, chlorocresols, chlorodimethylphenols, bromophenols, bromonaphthols, iodophenols; the mercaptophenols, the phenol aldehydes, such as hydroxybenzaldehydes, dihydroxybenzaldehydes, dihydroxymethoxybenzaldehydes, hydroxynaphthaldehydes; the phenol acids, such as hydroxybenzoic, phloretic, hydroxymandelic, and hydroxynaphthoic acids.

The reaction of the inorganic support with the organic compound having at least one alcohol or phenol function and at least one function reactive with the enzyme in order to give the ester bond is carried out at a temperature between room temperature and the boiling point of the medium, depending on the reactivity of the products used. The water formed due to reaction may remain in the medium without disadvantage, or else be eliminated. Preferably, one operates at boiling temperatures since the reaction is faster and proceeds with elimination of the water, which makes it possible to control the reaction time.

If the organic compound is liquid, in order to have a dispersion of the support, it is necessary to use an excess of the organic compound, namely, an amount of organic compound greater than 40 ml. per 100 g. of support.

In the event that the organic compound is solid or even liquid, it is possible to effect the reaction in the presence of a solvent for the organic compound. This solvent should be chemically inert towards the support and the organic compound and possibly form, upon boiling, an azeotrope with the water formed during the reaction. By way of example, mention may be made of dimethylformamide, xylene, and dioxan. The amount of organic compound is at least equal to that which corresponds to one alcohol or phenol function for one hydroxyl group of the support and the amount of solvent should be sufficient to wet the inorganic support.

Whether or not one operates in the presence of a solvent, after reaction, the grafted support is separated from the medium, washed with a solvent for the organic compound, and possibly dried if it is to be stored.

Any enzyme can be fixed on the supports, particularly the oxido-reductases, such as glucose oxidase, d-amino-acid-oxidase, lactate deshydrogenase, peroxidase, and catalase; the transferases, such as aspartate aminotransferase, aspartate acetyltransferase, hexokinase; the hydrolases, such as lipase, phospholipase, acetylcholinesterase, pectinase, phosphatase, amylase, maltase, cellulase, invertase, acylase, pepsin, papain, rennin, trypsin, chymotrypsin, asparaginase, urease, arginase, ribonuclease, lactase, bromelin, and penicillin amidase; the lyases, such as aspartase and fumerase; the isomerases, such as glucose isomerase and lactate racemase; and the ligases, such as asparagine synthetase, glutamine synthetase, and pyruvate carboxylase.

Depending on the reactive function of the graft, the enzyme may react, either directly or after activation of the graft, by any known methods. Thus, for instance, an aminated graft can be activated by diazotation or reaction with a polyaldehyde or a carbodiimide; a sulfhydryl graft can be activated by reaction with 2,2'-dithiodipyridine; a carboxyl graft can be activated by reaction with a carbodiimide. This activation is generally carried out by dispersion of the grafted support in an aqueous solution of an excess of reagent with respect to the group to be activated, at a pH and a temperature compatible with the reaction, followed by separation and washing of the support.

The fixing of the enzyme is effected by any known method, either in the cold in aqueous solution buffered in accordance with the pH which is most compatible with the enzyme, or in the heat in aliphatic, cycloaliphatic, or aromatic hydrocarbons, in accordance with the process of French Pat. No. 2,278,702.

The enzyme-support complexes obtained are stable and resistant to the factors of denaturization, pH and temperature and can be used both batchwise and continuously, without losing their enzymatic activity.

These complexes may be employed in affinity chromatography and in analytical and industrial enzymatic catalysis, especially in the food, pharmaceutical, or phytosanitary industries.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLE 1

50 g. of a silica in the form of microballs of a particle size of 100 to 200 $\mu m$, a specific surface of 25 $m^2/g$. (square meters per gram), an average pore diameter of 1250 Å (Angstroms), a pore volume of 1 ml./g., are added to 300 ml. of mono-ethanolamine. The dispersion is heated to the boiling point and then held at this temperature for 3 hours, with progressive elimination of 150 ml. of ethanolamine and of the water formed. After cooling, the silica is filtered, washed with 300 ml. of acetone; and then dried in the oven at 80° C. The product obtained contains 0.21 percent by weight of carbon and 0.1 percent by weight of nitrogen, determined by microanalysis.

The grafted silica obtained is treated with 250 ml. of a 4 weight percent solution of glutaraldehyde in 0.1 M (molar) phosphate buffer of a pH of 8, with agitation at room temperature for 2 hours. The treated grafted silica is then filtered, and then washed with 100 ml. of 0.1 M phosphate buffer, having a pH of 8.

The above treated grafted silica is then washed with 400 ml. of 0.05 M acetate buffer, having a pH of 4.5, and then dispersed in 250 ml. of 0.05 M acetate buffer, having a pH of 4.5, containing 4 percent by weight of lactase enzyme in solution. The dispersion is kept under agitation at room temperature for 15 hours. The enzyme-support complex formed is removed by filtration and then washed with 250 ml. of 0.05 M acetate buffer, having a pH of 4.5.

The enzymatic activity of the resulting complex is determined by contacting 1 g. of complex with 10 ml. of a lactose solution of 40 g./l. in 0.05 M acetate buffer, pH 4.5, at 55° C., and agitating for 10 minutes. The complex is removed by filtration and the glucose formed by enzymatic action is determined in the filtrate. The enzymatic activity of the complex is 78 U/g. (the unit "U" being the amount of complex which hydrolyzes one micromol of lactose per minute).

The enzymatic activity of the enzyme in solution, before attachment and after attachment, is determined by adding 1 ml. of the enzyme solution to 10 ml. of a 40 g./l. lactose solution in 0.05 M acetate buffer, having a pH of 4.5, at 55° C., maintaining the solution under agitation for 5 minutes, and then stopping the reaction by placing the receptacle in boiling water for 5 minutes. After cooling, the glucose formed is determined. By difference between the two activities, the activity which has disappeared during the attachment is obtained.

The ratio between the activity of the immobilized enzyme and the activity which has disappeared from the solution gives the immobilization yield of the lactase, which is 55 percent.

By way of comparison, Example 1 is repeated with a support grafted by an aminosilane, obtained in the following manner:

50 g. of the same silica balls as used in Example 1 are placed in suspension in 250 ml. of xylene containing 5 g. of γ-aminopropyltriethoxysilane. The suspension is heated at the boiling point for 3 hours. After cooling, the silica is removed by filtration, washed with 300 ml. of acetone, and then dried at 80° C. By analysis, it is found that the product obtained contains 0.70 percent by weight of carbon and 0.18 percent by weight of nitrogen.

After the fixing of the lactase, the complex formed has an enzymatic activity of 80 U/g. and the immobilization yield is only 22 percent.

It is found that the two complexes have substantially the same activity, but in order to obtain this activity, it is necessary to use only one-quarter as much enzyme with the support in accordance with the enzyme-support complex of the invention.

THE USE OF THE COMPLEX OF THE INVENTION 10 g. of complex of the invention as described in Example 1 are placed in a column of 2.5 cm. diameter, maintained at 55° C.

A 40 g./l. solution of lactose in an 0.05 M acetate buffer, having a pH of 4.5, is continuously percolated through the column at the rate of 200 ml. per hour. The percentage of enzymatic hydrolysis of the lactose into glucose, measured on the solution emerging from the column, is 80 percent. After 500 hours of continuous operation, the hydrolysis percentage is still maintained at 80 percent. This shows the excellent stability of the lactase-support complex of the invention.

EXAMPLE 2

Example 1, above, is repeated, but without eliminating any of the ethanolamine or the water formed in the preparation of the grafted support. The resulting grafted support contains 0.2 percent by weight of carbon and 0.1 percent by weight of nitrogen.

It is found that the water which has remained in the reaction medium has no effect on the grafting on the support.

The lactase-support complex obtained has an enzymatic activity of 80 U/g. and the immobilization yield is 55 percent.

EXAMPLE 3

A lactase-support complex is prepared in the same manner as in Example 1, but with a silica of a particle size of about 200 μm to 1 mm.

The enzymatic activity of the complex is 64 U/g. and the immobilization yield is 55 percent.

EXAMPLE 4

Example 1, above, is repeated, but the silica is replaced by an alumina having a particle size of 100 to 200 μm, a specific surface of 154 m$^2$/g., an average pore diameter of 350 Å, and a pore volume of 1.18 ml./g. Analysis shows that the grafted alumina contains 1.98 percent by weight of carbon and 0.87 percent by weight of nitrogen.

The lactase-support complex obtained has an enzymatic activity of 90 U/g. and the immobilization yield is 35 percent.

EXAMPLE 5

50 g. of silica having a particle size of 100-200 μm, a specific surface of 25 m$^2$/g., an average pore diameter of 1250 Å, and a pore volume of 1 ml./g., are dispersed in 300 ml. of dimethylformamide in which 20 g. of 5-amino-1-pentanol are dissolved. The dispersion is heated to the boiling point and held at this temperature for 3 hours, with progressive elimination of 150 ml. of dimethylformamide and of the water formed due to reaction. After cooling, the resulting grafted silica is filtered, washed with 300 ml. of dimethylformamide, and then with 150 ml. of acetone, and finally dried at 80° C. Analysis shows that the product obtained contains 0.35 percent by weight of carbon and 0.09 percent by weight of nitrogen.

The grafted silica obtained is treated with 250 ml. of a solution of 4 percent by weight of glutaraldehyde in 0.1 M phosphate buffer, having a pH of 8, with agitation, at room temperature, for 2 hours. The treated grafted silica is then filtered and then washed with 100 ml. of 0.1 M phosphate buffer, of pH 8.

The resulting treated grafted silica is then washed with 400 ml. of 0.05 M acetate buffer, of pH 4.5, and then dispersed in 250 ml. of 0.05 M acetate buffer, of pH 4.5, containing in solution 4 percent by weight of lactase. The dispersion is kept under agitation, at room temperature, for 15 hours. The enzyme-support complex formed is removed by filtration and then washed with 250 ml. of 0.05 M acetate buffer, of pH 4.5. It has an enzymatic activity of 40 U/g. and the immobilization yield is 45 percent.

EXAMPLE 6

For the preparation of the grafted support, one proceeds in the same manner as in Example 1, but using a silica having a particle size of 100 to 200 μm, a specific surface of 100 m$^2$/g., an average pore diameter of 300 Å, and a pore volume of 1 ml./g. The grafted silica obtained contains 0.95 percent by weight of carbon and 0.38 percent by weight of nitrogen.

As compared with Example 1, it is noted that the use of silica of greater specific surface makes it possible to obtain a larger number of grafts.

The grafted silica obtained is treated with 250 ml. of 4 weight percent glutaraldehyde solution in a 0.1 M phosphate buffer, of pH 8, with agitation at room temperature for 2 hours. After filtration, the modified grafted silica obtained is washed with 100 ml. of 0.1 M phosphate buffer, of pH 8. 10 g. of the grafted silica are then washed with 400 ml. of 0.02 M phosphate buffer, of pH 7, and then dispersed in 500 ml. of 0.02 M phosphate buffer, of pH 7, containing in solution 1 percent penicillin amidase. The dispersion is kept under agitation at room temperature for 15 hours. The penicillin amidase-support complex formed is separated by filtration and then washed with 50 ml. of 0.02 M phosphate buffer, of pH 7.

The enzymatic activity of the penicillin amidase-support complex obtained is determined by contacting 0.5 g. of complex with 40 ml. of a 20 g./l. penicillin G solution in 0.1 M phosphate buffer, of pH 7.5, at 30° C., for 30 minutes. The complex is then removed by filtration and the 6-amino-penicillanic acid (6-APA) formed determined in the filtrate. The enzymatic activity of the complex is 50 U/g. (the unit "U" is the amount of complex which hydrolyzes 1 mircomol of penicillin G per minute).

The enzymatic activity of the enzyme in solution, before and after mixing, is determined by adding 1 ml. of the enzyme solution to 10 ml. of a 20 g./l. penicillin G solution in 0.1 M phosphate buffer, of pH 7.6, keeping under agitation at 30° C. for 30 minutes, and then determining the 6-amino-penicillanic acid formed.

The immobilization yield of the enzyme is 70 percent.

USE OF THE COMPLEX OF THE INVENTION 1 g. of the complex of Example 6 is placed in a column of a diameter of 1 cm. A 20 g./l. solution of penicillin G in 0.1 M phosphate buffer, of pH 7.6, is percolated through the column continuously at room temperature at the rate of 50 ml per hour. The percentage of hydrolysis of the penicillin G to 6-APA, measured on the solution emerging from the column, is 40 percent. After 300 hours of operation, the percentage of hydrolysis is still 40 percent. This shows the good stability of the penicillin amidase-support complex.

EXAMPLE 7

50 g. of silica having a particle size of 100 to 200 μm, a specific surface of 25 m²/g., an average pore diameter of 1250 Å, and a pore volume of 1 ml./g. are dispersed in 300 ml. of dimethylformamide in which 20 g. of p-aminophenol are dissolved. The resulting dispersion is heated to the boiling point and kept at this temperature for 3 hours, with progressive elimination of 150 ml. of dimethylformamide and of the water formed due to reaction. After cooling, the resulting silica is filtered, washed with 300 ml. of dimethylformamide, and then with 150 ml. of acetone, and finally dried at 80° C. Analysis shows that the product obtained contains 0.31 percent by weight carbon and 0.06 percent by weight nitrogen.

The resulting grafted silica is treated with 250 ml. of a 4 percent by weight solution of glutaraldehyde in 0.1 M phosphate buffer, of pH 8, with agitation, at room temperature, for 2 hours, then filtered, and finally washed with 100 ml. of 0.1 M phosphate buffer, of pH 8. A penicillin-amidase support complex is prepared from this grafted silica as in Example 6, above. It has an enzymatic activity of 16 U/g. and the immobilization yield is 65 percent.

EXAMPLE 8

10 g. of the same grafted silica as used in Example 7, above, are treated with 200 ml. of 1/10 N hydrochloric acid and 100 ml. of 1/10 M NaNO$_2$, with agitation, at 0° C., for 3 hours. After filtration and washing with 500 ml. of cold water, the diazotized grafted silica is dispersed in 50 ml. of a 4 percent solution of lactase by weight in 0.05 M acetate buffer, or pH 4.5. The dispersion is maintained under agitation at 4° C. for 3 hours. The lactase-support complex formed is separated by filtration and then washed with the same acetate buffer.

The enzymatic activity of the complex obtained is 71 U/g. and the immobilization yield is 20 percent.

EXAMPLE 9

10 g of the same diazotized grafted silica as in Example 8, above, are dispersed in 200 ml. of a solution of acylase of 1 percent by weight in 0.1 M TRIS buffer, of pH 8. The dispersion is maintained under agitation at 4° C. overnight. The acylase-support complex formed is filtered and then washed with the same TRIS buffer.

The enzymatic activity of the complex is determined by contacting 500 mg. of complex with 50 ml. of an 0.4 weight percent solution of N-acetyl-DL-methionine in 0.1 M TRIS buffer, of pH 8, containing 5·10$^{-4}$ M of cobalt chloride, at 37° C., and agitated for 30 minutes. The complex is filtered and the L-methionine formed is determined in the filtrate.

The enzymatic activity of the complex is 10 U/g. (the unit "U" being the amount of complex which transforms 1 micromol of N-acetyl-DL-methionine per minute).

The enzymatic activity of the acylase in solution, before and after fixing, is determined by adding 0.1 ml. of the enzyme solution to 5 ml. of an 0.4 weight percent solution of N-acetyl-DL-methionine in 0.1 M TRIS buffer, of pH 8, containing 5·10$^{-4}$ mols of cobalt chloride. The mixture is maintained for 30 minutes at 37° C., whereupon the reaction is stopped by immersing the receptacle in boiling water for 3 minutes. After cooling, the L-methionine formed is determined.

The immobilization yield of the acylase, that is to say, the ratio between the activity of the complex and the activity which has disappeared, is 50 percent.

EXAMPLE 10

An acylase-support complex is prepared in the same manner as in Example 9, above, but with a silica of a particle size of 30 to 100 μm. The enzymatic activity of the complex is 10.5 U/g. and the immobilization yield is 50 percent.

Use of the Complex of the Invention 30 g. of complex of Example 10 are placed in a column of 1 cm. diameter and 90 cm. in height. 300 ml. of 0.1 M TRIS buffer, of pH 8, are passed through the column at room temperature in 2 hours, whereupon 2 ml. of the same buffer are injected containing 10 μmoles of DL-methionine, and finally 0.1 M TRIS buffer, of pH 8, is passed through at the rate of 10 ml./hour. The ultraviolet spectrometry of the liquid emerging from the column shows that there is a separation of the D-methionine and the L-methionine. There are collected in succession, a fraction of 3 ml. containing the D-methionine, a fraction of 4 ml. containing a mixture of D and L-methionines, and a fraction of 3 ml. containing the L-methionine.

EXAMPLE 11

50 g. of silica balls of a particle size of 100 to 200 μm, a specific surface of 23 m²/g., an average pore diameter of 1330 Å, and a pore volume of 0.96 ml./g. are added to 200 ml. of xylene containing 30 g. of chloro-2-ethanol. Heating is effected to the boiling point, this temperature being maintained for 4 hours. After cooling, the silica is filtered, washed with 300 ml. of acetone, and then dried in the oven at 80° C. by microanalysis, it is determined that the product obtained contains 0.16 percent by weight of carbon and 0.20 percent by weight of chlorine.

The grafted silica obtained is dispersed in 400 ml. of a 1 percent solution by weight of urease in an 0.1 M phosphate buffer, of pH 6.5, then left with agitation at room temperature for 20 hours. The urease-support complex formed is filtered and then washed with 250 ml. of 0.1 M phosphate buffer, of pH 6.5.

The enzymatic activity of the complex is determined by contacting 100 mg. of complex with 20 ml. of a 30 g./l. urea solution in 0.1 M phosphate buffer, of pH 7, at 37° C., and agitating for 3 minutes. The complex is then separated by filtration and the ammonia formed is neutralized by the addition of 20 ml. of 0.1 N hydrochloric acid to the separated solution. The excess acid is titrated with 0.1 N caustic soda. The enzymatic activity of the complex is 1500 U/g. (the unit "U" being the amount of complex which liberates 1 micromol of ammonia per minute).

The enzymatic activity of the urease in solution, before and after fixing, is determined by adding 0.5 ml. of the enzyme solution to 4 ml. of a 30 g./l. solution of urea in 0.1 M phosphate buffer, of pH 7, at 37° C., agitating for 3 minutes, and then stopping the reaction by adding 5 ml. of 0.1 N hydrochloric acid. The excess acid is then determined by neutralization with 0.1 N sodium hydroxide. By difference between the two activities, one obtains the activity which has disappeared during the fixing of the enzyme.

The ratio between the activity of the immobilized enzyme and the activity which has disappeared from the solution gives the immobilization yield of the urease, which is 60 percent.

EXAMPLE 12

5 g. of a grafted silica, identical to that of Example 11, above, are dispersed in 50 ml. of 0.05 M phosphate buffer, of pH 7, containing 100 mg. of catalase in solution, whereupon the dispersion obtained is kept under agitation for 4 hours at room temperature. The catalase-support complex formed is filtered and then washed with 50 ml. of 0.05 M phosphate buffer, of pH 7.

The enzymatic activity of the complex is determined as follows: 10 mg. of the complex are added to 5 ml. of an 0.02 M solution of hydrogen peroxide in 0.05 M phosphate buffer, of pH 7, and then maintained in dispersion by agitation for 2 minutes at 25° C. The decomposition reaction of the hydrogen peroxide is stopped by addition of 3 drops of concentrated sulfuric acid and the excess hydrogen peroxide determined with the use of an aqueous solution of potassium permanganate of $5 \cdot 10^{-3}$ M. The activity of the complex is 2280 U/g. (the unit "U" is the amount of complex which decomposes 1 micromol of hydrogen peroxide per minute).

The activity of the enzyme in solution is also determined before and after fixing. 0.2 ml. of the enzyme solution are added to 5 ml. of an 0.02 M hydrogen peroxide solution in 0.05 M phosphate buffer, of pH 7, whereupon the mixture is agitated for 2 minutes at 25° C. 3 drops of concentrated sulfuric acid are then added to stop the reaction and the hydrogen peroxide in excess is determined with the use of a $5 \cdot 10^{-3}$ M solution of potassium permanganate.

The immobilization yield of the catalase, that is to say, the ratio between the activity of the complex and the activity which has disappeared, is 11 percent.

EXAMPLE 13

50 g. of silica balls of a particle size of 100 to 200 μm, a specific surface of 23 m²/g., an average pore diameter of 1330 Å, and a pore volume of 0.96 ml./g. are added to 250 ml. of dimethylformamide containing 15 g. of 4-hydroxybenzaldehyde. The dispersion obtained is heated to the boiling point and kept at this temperature for 4 hours. After cooling, the silica is filtered, washed with 250 ml. of dimethylformamide and then 150 ml. of acetone, and finally dried in an oven at 80° C.

By microanalysis, it is found that the product obtained contains 0.20 percent by weight of carbon.

Urease is immobilized on the grafted silica in the manner described in Example 11, above.

The urease-support complex has an enzymatic activity of 1400 U/g. and the immobilization yield is 55 percent.

EXAMPLE 14

Catalase is immobilized on a grafted silica identified to that of Example 13, in the same manner as described in Example 12, above.

The catalase-support complex obtained has an enzymatic activity of 2250 U/g. and the immobilization yield is 10 percent.

EXAMPLE 15

5 g. of a grafted silica, identical to that of Example 13, above, are dispersed in 200 ml. of a 1 percent solution of trypsin in 0.1 M TRIS buffer, of pH 7.8. The dispersion obtained is then kept under agitation for 4 hours at room temperature. The trypsin-support complex formed is filtered and then washed with 50 ml. of 0.1 M TRIS buffer, of pH 7.8.

The enzymatic activity of the complex is determined in the following manner: 10 mg. of complex are contacted with 10 ml. of 0.2 M TRIS buffer, of pH 7.8, containing 25 mmols per liter of calcium chloride and with 0.2 ml. of a solution containing 12 mmols per liter of benzoylarginine-p-nitranilide at 25° C., with agitation for 2 minutes. The complex is filtered and the p-nitraniline formed and contained in the filtrate is determined by colorimetry.

The enzymatic activity of the complex is 13.8 U/g. (the unit "U" is the amount of complex which hydrolyzes 1 micromol of benzoylarginine-p-nitranilide per minute at 25° C. and a pH of 7.8).

The enzymatic activity of the trypsin in solution, before and after fixing, is determined by adding 0.2 ml. of enzyme solution in 0.1 M TRIS buffer, of pH 7.8, to 2 ml. of 0.2 M TRIS buffer, of pH 7.8, containing 22 mmols per liter of calcium chloride, to which there has been added 0.2 ml. of a 12 mmol per liter solution of benzoylarginine-p-nitranilide, the solution obtained being kept at 25° C. for 15 minutes and the paranitraniline formed being then determined.

The ratio between the activity of the immobilized enzyme and the activity which has disappeared from the solution gives the immobilization yield of the trypsin, which is 78 percent.

EXAMPLE 16

50 g. of the same grafted silica as in Example 13 are dispersed in 250 ml. of 0.05 M acetate buffer, pH 4.5, containing 4 percent by weight of lactase in solution. The dispersion is maintained under agitation at room temperature for 15 hours. The enzyme-support complex formed is separated by filtration and then washed with 1250 ml. of 0.05 M acetate buffer, of pH 4.5.

The enzymatic activity and the immobilization yield for the above complex, determined as in Example 1, are 85 U/g. and 45 percent, respectively.

USE OF THE COMPLEX OF THE INVENTION 5 g. of complex of Example 16 are placed in a column of a diameter of 2.5 cm. A 2 weight percent solution of glutaraldehyde in 0.1 M phosphate buffer, of pH 8, is percolated through the column at the rate of 100 ml. per hour for 3 hours at room temperature, whereupon 100 ml. of phosphate buffer are passed through in 1 hour. Thereupon, a 40 g./l. solution of lactose in 0.05 M acetate buffer, of pH 4.5, is percolated continuously at 55° C., at the rate of 100 ml. per hour.

The percentage of hydrolysis of lactose into glucose, measured on the solution emerging from the column, is 69 percent. After 200 hours of continuous operation, the percentage of hydrolysis is unchanged. This shows the excellent stability of the lactase-support complex.

EXAMPLE 17

30 g. of silica balls of a particle size of 100 to 200 μm, a specific surface of 23 m²/g., an average pore diameter of 1330 Å, and a pore volume of 0.96 ml./g. are added to 100 ml. of mercaptoethanol. The resultant dispersion is heated to the boiling point and then maintained at this temperature for 4 hours. After cooling, the silica is filtrated, washed with 200 ml. of acetone, and then dried at 80° C.

By microanalysis, it is found that the product obtained contains 0.25 percent by weight of carbon and 0.32 percent by weight of sulfur.

The grafted silica obtained is washed with 250 ml. of an 0.3 M sodium chloride solution in 0.1 M TRIS buffer, of pH 8, containing 1 mmol of EDTA at room temperature, whereupon the silica is filtered and then contacted and agitated, at room temperature for 30 minutes, with 500 ml. of the same TRIS/NaCl/EDTA buffer containing 30 mmol of 2,2'-dithiodipyridine. The silica is then filtered, and washed with 250 ml. of 0.1 M phosphate buffer, of pH 7.

The grafted silica is then dispersed in 250 ml. of a 1 percent by weight solution of urease in 0.1 M phosphate buffer, of pH 6.5, then left with agitation at room temperature for 20 hours. The urease-support complex formed is filtered and then washed with 150 ml. of 0.1 M phosphate buffer, of pH 6.5.

The enzymatic activity of the complex and the immobilization yield, determined as in Example 11, are 1500 U/g. and 52 percent, respectively.

EXAMPLE 18

30 g. of silica balls of a particle size of 100 to 200 μm, a specific surface of 23 m²/g., an average pore diameter of 1330 Å, and a pore volume of 0.96 ml./g. are added to 100 ml. of dioxan containing 25 ml. of hydroxy-3-propionic acid. The dispersion obtained is heated to the boiling point and then kept at this temperature for 4 hours. After cooling, the silica is filtered, washed with 200 ml. of acetone, and then dried in the oven at 80° C. The product obtained contains 0.10 percent by weight of carbon.

The grafted silica obtained is dispersed in 300 ml. of 0.05 M phosphate buffer, of pH 5.5, containing 600 ml. of catalase in solution. The agitated dispersion is maintained at room temperature for 4 hours. The catalase-support complex formed is filtered and then washed with 250 ml. of 0.05 M phosphate buffer, of pH 5.5.

The enzymatic activity of the complex is 1500 U/g. and the immobilization yield is 10 percent.

EXAMPLE 19

30 g. of the same dried grafted silica as in Example 18 are dispersed in 300 ml. of 0.05 M acetate buffer, of pH 4.5, containing in solution 3 g. of 1-cyclohexyl-3-(2-morpholinoethyl)carbodiimide metho-p-toluene sulfonate. The dispersion is kept at room temperature for 3 hours with agitation. The silica is then filtered and then washed with 500 ml. of distilled water.

Trypsin is fixed to the product obtained, above, in the same manner as in Example 15, above.

The complex formed has an enzymatic activity of 13.8 U/g. and the immobilization yield is 79 percent.

As will be apparent to those skilled in the art from the foregoing specification, other inorganic supports, including those discussed hereinabove, may be employed in each of the foregoing examples. Similarly, other organic grafting compounds disclosed hereinabove may be employed in place of those utilized in the foregoing examples. Also, instead of the enzymes employed in the foregoing examples, any of the many enzymes discussed in the present specification may be employed.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed.

What is claimed is:

1. An enzyme-support complex comprising an enzyme fixed by covalent bond to a grafted inorganic support, said inorganic support having surface hydroxyl groups, said enzyme being bound to at least one reactive function selected from the class consisting of amine, halogen, sulfhydryl, aldehyde, and carboxyl functions, of an organic group selected from the class consisting of a linear or branched aliphatic radical whose chain contains between about 1 to 8 carbon atoms, a cyclane radical, an aryl radical and an alkylaryl radical; said organic group being grafted to said support by at least one ester bond obtained by reaction of at least one alcohol or phenol function of said organic group provided by an organic compound selected from the class consisting of an amino alcohol, a halo-alcohol, a mercapto-alcohol, an alcohol-aldehyde, an alcohol-acid, an amino-phenol, a halo-phenol, a mercapto-phenol, a phenol-aldehyde, and a phenol-acid with at least one hydroxyl group of the support.

2. An enzyme-support complex according to claim 1, wherein said aliphatic radical contains a member selected from the class consisting of nitrogen, sulfur atoms, and a phenyl group; and said aryl radical and said alkylaryl radical contain in ring and/or chain at least 1 nitrogen atom.

3. An enzyme-support complex according to claim 1, wherein said support is a member selected from the class consisting of brick, alkaline silicates, alkaline aluminosilicates, metallic oxides, and a silica.

4. An enzyme-support complex according to claim 1, wherein the enzyme is a member selected from the class consisting of oxido-reductases, transferases, hydrolases, lyases, isomerases, and ligases.

5. An enzyme-support complex according to claim 4, wherein the enzyme is a member selected from the class consisting of glucose oxidase, peroxidase, amylase, invertase, trypsin, urease, lactase, penicillin amidase, and glucose isomerase.

6. A process of obtaining an enzyme-support complex according to claim 1, comprising
   (a) dispersing said insoluble inorganic support in a medium containing said organic compound either in liquid form or dissolved in an organic solvent;
   (b) reacting at least said one alcohol or phenol function of said organic group with at least said one hydroxyl group of said inorganic support to obtain the formation of at least said one ester bond, at a temperature between room temperature and the boiling point of said medium; and
   (c) bonding said enzyme to the reactive function of said organic compound.

7. A process according to claim 6, wherein the support is a member selected from the class consisting of brick, alkaline silicates and aluminosilicates, metallic oxides, and silicas.

8. A process according to claim 6, wherein when said organic compound is liquid, the reaction is carried out by dispersing the support in an excess of the organic compound.

9. A process according to claim 6, wherein the amount of organic compound dissolved in a solvent is at least that which corresponds to one alcohol or phenol function for one hydroxy group of the support.

10. A process according to claim 6, wherein said enzyme immobilized is a member selected from the class consisting of oxido-reductases, transferases, hydrolases, lyases, isomerases, and ligases.

11. A process according to claim 6, wherein said enzyme reacts either directly or after activation of said reactive function.

12. A process according to claim 6, wherein said linear or branched aliphatic radical contains a member selected from the class consisting of nitrogen or sulfur atoms and a phenyl group; said aryl radical and said alkylaryl radical contain in ring and/or chain at least one nitrogen atom.

* * * * *

UNITED STATES PATENT AND TRADEMARK OFFICE
CERTIFICATE OF CORRECTION

PATENT NO. : 4,258,133

DATED : March 24, 1981

INVENTOR(S) : Bernard Mirabel et al.

It is certified that error appears in the above—identified patent and that said Letters Patent is hereby corrected as shown below:

Col. 9, line 63, change "identified" to -- identical --

Col. 10, line 44, change "1250 ml." to -- 250 ml. --

Signed and Sealed this

Eighteenth Day of August 1981

[SEAL]

Attest:

GERALD J. MOSSINGHOFF

Attesting Officer     Commissioner of Patents and Trademarks